United States Patent
Wang et al.

(10) Patent No.: US 11,197,855 B2
(45) Date of Patent: Dec. 14, 2021

(54) USE OF LIGUSTRAZINE NITRONE DERIVATIVES IN PREVENTION AND TREATMENT OF DIABETIC COMPLICATION DISEASES

(71) Applicant: QINGDAO HAILAN PHARMACEUTICALS CO., LTD., Qingdao (CN)

(72) Inventors: Yuqiang Wang, Qingdao (CN); Yewei Sun, Qingdao (CN); Lipeng Xu, Qingdao (CN); Mei Jing, Qingdao (CN); Zaijun Zhang, Qingdao (CN); Gaoxiao Zhang, Qingdao (CN); Pei Yu, Qingdao (CN); Peng Yi, Qingdao (CN)

( * ) Notice: Subject to any disclaimer, the term of this patent is extended or adjusted under 35 U.S.C. 154(b) by 112 days.

(21) Appl. No.: 16/602,714

(22) PCT Filed: May 25, 2018

(86) PCT No.: PCT/CN2018/000194
§ 371 (c)(1),
(2) Date: Nov. 22, 2019

(87) PCT Pub. No.: WO2018/218961
PCT Pub. Date: Dec. 6, 2018

(65) Prior Publication Data
US 2020/0155548 A1    May 21, 2020

(30) Foreign Application Priority Data
May 27, 2017    (CN) .......................... 201710392539.X

(51) Int. Cl.
*A61K 31/4965*    (2006.01)
*A61P 3/10*    (2006.01)
*A61K 31/519*    (2006.01)
*A61K 45/06*    (2006.01)

(52) U.S. Cl.
CPC ............ *A61K 31/4965* (2013.01); *A61P 3/10* (2018.01); *A61K 31/519* (2013.01); *A61K 45/06* (2013.01)

(58) Field of Classification Search
CPC .. A61K 31/4965; A61K 31/519; A61K 45/06; A61P 3/10; A61P 25/00; A61P 13/12; A61P 27/06; A61P 27/12; A61P 27/10
USPC ...................................................... 514/252.1
See application file for complete search history.

(56) References Cited

U.S. PATENT DOCUMENTS

2011/0034485 A1 *    2/2011    Wang ........................ A61P 3/10
514/256
2012/0115874 A1 *    5/2012    Wang ...................... A61P 25/08
514/249

OTHER PUBLICATIONS

Wikipedia, ACE inhibitor, Feb. 2016, p. 1-11. (Year: 2016).*

* cited by examiner

*Primary Examiner* — Taylor V Oh
(74) *Attorney, Agent, or Firm* — Panterrain IP Law; Charles Liu

(57) ABSTRACT

A use of of ligustrazine nitrone derivatives and a pharmaceutical composition thereof in the preparation of medicine for preventing and treating diabetic complication diseases. The ligustrazine nitrone derivatives can be prepared into various dose forms together with drug carriers.

9 Claims, 4 Drawing Sheets

Table 1. Number of occurrences and time of appearance of retinopathy in diabetic nephropathy model rats

| Group | Retinopathy Number of cases | Time of Retinopathy (nth day from the date of successful modeling) | | | | | | |
|---|---|---|---|---|---|---|---|---|
| | | #1 | #2 | #3 | #4 | #5 | #6 | #7 |
| Control | 0 | / | / | / | / | / | / | / |
| Model | 6 | 27 | 28 | 33 | 36 | 37 | 37 | / |
| TBN (10 mg/kg) | 3 | 23 | 24 | 28 | / | / | / | / |
| TBN (30 mg/kg) | 6 | 36 | 39 | 40 | 40 | 41 | 41 | / |
| TBN (60 mg/kg) | 2 | 39 | 42 | / | / | / | / | / |
| TN-2 (30 mg/kg) | 3 | 24 | 38 | 42 | / | / | / | / |
| Losartan(10 mg/kg) | 3 | 36 | 36 | 39 | / | / | / | / |
| TBN (60 mg/kg) + Losa.(10 mg/kg) | 6 | 31 | 32 | 33 | 36 | 36 | 38 | / |

FIG. 5

USE OF LIGUSTRAZINE NITRONE DERIVATIVES IN PREVENTION AND TREATMENT OF DIABETIC COMPLICATION DISEASES

FIELD OF THE INVENTION

The present invention relates generally to the field of medicine and, more particularly, to the use of ligustrazine nitrone derivatives and pharmaceutical composition thereof in prevention and treatment of diseases of diabetic complications.

BACKGROUND OF THE INVENTION

Diabetes are metabolic diseases characterized by hyperglycemia due to defects in insulin secretion or impaired insulin action. Sustained hyperglycemia and long-term metabolic disorders can cause damages or even dysfunction and failure to the systemic tissues and organs, especially eyes, kidneys, cardiovascular and nervous system, and in severe cases, can cause complications of ketoacidosis, such as electrolyte imbalance and acid-base balance disorders, and hyperosmolar coma dehydration.

Diabetic Kidney Disease (DKD) is one of the most important microvascular complications with clinical features of proteinuria, progressive renal impairment, hypertension, edema, and severe renal failure in the late stage. DKD is currently the leading cause of end-stage renal disease, with approximately 30% to 40% of diabetic patients suffering from kidney disease. According to IDF, the global prevalence of diabetes in 2013 was 382 million, and may grow to 592 million in 25 years.

So far, the mechanism for the development of DKD has not been fully clarified. However, it is currently believed that the pathogenesis of DKD is related to the disorder of glucose metabolism and the resulting non-enzymatic glycation, activation of the polyol pathway, activation of protein kinase C, disorders of lipid metabolism, renal hemodynamic changes caused by hypertension, and oxidation stimulation, vasoactive substances and cytokines, genetics. It is reported that mitochondria are the main source of intracellular reactive oxygen species (ROS) and an important participant in the endogenous apoptotic pathway. The excessive synthesis of ROS may be the starting point in the pathogenesis of diabetes and its complications, and blocking or clearance of ROS can reduce the increase in urinary protein excretion, glomerular sclerosis, and tubulointerstitial fibrosis caused by diabetic nephropathy (Michael Brownlee, Nature, 2001, 414: 813-820).

Diabetic eye disease is also one of the common complications of diabetes. During the course of diabetes, most of the tissues of the eyes of the patient of diabetes are affected, resulting in ocular lesions of varying degrees and different symptoms. Eye diseases caused by diabetes mainly include retinopathy, cataracts and glaucoma.

Ligustrazine (Tetramethylpyrazine) is one of the main active ingredients of traditional Chinese medicine Chuanxiong (*Ligusticum wallichii*). It is widely used in the treatment of diseases such as cardio-cerebral vascular disease, nephropathy, retinopathy, and optic nerve ischemic eye disease. Previous studies have confirmed that ligustrazine has pharmacological activities including anti-thrombosis, anti-ischemic reperfusion, protection of cardio-cerebral vascular system, liver, and kidney (Modern Chinese Medicine in China, 2016, 18 (10): 1364-1370). The structure of tetramethylpyrazine is as follows:

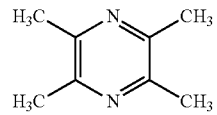

Tetramethylpyrazine can exert renal cell cytoprotection through anti-apoptosis, anti-inflammatory, anti-oxidation and other ways, thereby reducing functional damage of the kidney. Yang et al (Phytomedicine, 2011, 18 (13): 1148-1152), in their studies of rat diabetic nephropathy induced by streptozotocin, showed that tetramethylpyrazine can significantly improve renal function and down-regulate blood glucose and urine protein exclusion in rats with diabetic nephropathy. The mechanism of action may be related to the down-regulation of VEGF in kidney tissue by tetramethylpyrazine. Gong et al (Archives of Toxicology, 2015, 89 (7): 1057-1070) demonstrated that tetramethylpyrazine also has protective activity against sodium arsenite-induced damage to human renal proximal tubule cells, and its mechanism is related to inhibition of ROS production, increase in GSH level, increase of cytochrome C oxidase activity, restoration of mitochondrial membrane potential, improvement of mitochondrial dysfunction and reduction of protein expression of β-catenin, NF-κB, p38 MAPK, TNF-α, COX-2, thereby blocking cell apoptosis. At the same time, Gong et al also confirmed in their other studies on tetramethylpyrazine (Am J Nephrol, 2013, 37 (3): 199-207) that tetramethylpyrazine may be protective in kidney damage model induced by contrast agent through inhibition of p38 MAPK protein expression.

Clinical studies have shown that tetramethylpyrazine has certain therapeutic effect on diabetic nephropathy and has high safety. Yang Lin et al (Chinese Journal of Information on TCM, 2011, 18 (8): 26-29) systematically evaluated the clinical study of tetramethylpyrazine injection in the treatment of diabetic nephropathy, and the results showed that, the combined application of tetramethylpyrazine, as compared with the conventional treatment group, can reduce 24 h urinary albumin excretion rate, 24 h total urine proteins and 24 h urine protein quantitation in patients with diabetic nephropathy, but its effect on reduction of blood urea nitrogen, diastolic blood pressure and systolic blood pressure is not significant. At the same time, there was no indication of serious adverse reaction during the use, which suggests that tetramethylpyrazine injection has certain curative effect on patients with diabetic nephropathy. Chen Yingjun et al (China Practical Medicine, 2013, 8 (23): 178-179) found that, in the treatment of patients with type 2 diabetes with peripheral neuropathy, large doses of tetramethylpyrazine injection (360-400 mg/d) via intravenous drops with 12 d as one course of treatment, the total effective rate of treatment is as high as 95%, while the conventional dose of tetramethylpyrazine injection group (80 mg/d) is 82.93%. The total effective rate of the high dose group is higher than that of the conventional dose group, without increase of tadverse reactions.

Tetramethylpyrazine is also widely used in the treatment of ophthalmic diseases. At present, tetramethylpyrazine is clinically applied to treat eye diseases, such as diabetic retinopathy, retinal vascular occlusion, ischemic retinopathy, and glaucoma. Deng Xinguo et al used intraperitoneal injection of tetramethylpyrazine hydrochloride to observe the pharmacokinetics of retinal tissue in rabbit eyes, and their study showed that after intraperitoneal injection of tetramethylpyrazine, the drug can enter the retinal tissue through the blood-retinal barrier. This result provides an experimental basis for the treatment of fundus diseases by systemic administration of tetramethylpyrazine. Some researchers divided 40 patients with diabetic retinopathy into 20 patients in the treatment group and 20 patients in the control group. In the treatment group, the patients were intravenously instilled with puerarin injection, and took orally traditional Chinese medicine of Zishen Jianpi Huayu Recipe, and applied with electronically controlled tetramethylpyrazine ion. In the control group, the patients were intravenously instilled with puerarin injection, and took orally traditional Chinese medicine of Zishen Jianpi Huayu Recipe. The changes of the two groups before and after treatment and the fundus were observed. The results showed that the total effective rate was 86.84% in the treatment group and 67.50% in the control group. The therapeutic effect of the treatment group was significantly better than that of the control group. The difference between the two groups was statistically significant (Wang Yan, Chinese Journal of Ophthalmology, 2004). The mechanism of action of tetramethylpyrazine in the treatment of fundus diseases is generally considered to be related to improving blood rheology, inhibiting cell proliferation, scavenging free radicals, inhibiting apoptosis and antagonizing calcium ions.

In summary, tetramethylpyrazine may alleviate diabetic nephropathy and fundus diseases through anti-apoptosis, anti-inflammatory and anti-oxidation, and shows some therapeutic effects on diabetic nephropathy in clinical research, but its free radicals scavenging ability is insufficient, and thus the treatment effect of it cannot meet the clinical needs.

Nitrone derivatives are a class of compounds with strong free radical scavenging ability with strong scavenging effects on various active free radicals. It is found that nitrone derivatives have certain therapeutic effects on various diseases induced by free radicals, such as cancer, stroke, and Parkinson's disease. Based on the clinical application of tetramethylpyrazine in the treatment of diabetic nephropathy and fundus diseases, and the strong free radical scavenging effect of nitrone compounds, we have creatively synthesized ligustrazine nitrone derivatives TBN and TN-2. Studies have found that the ligustrazine nitrone derivatives have a significant protective effect on diabetic nephropathy rat model, and can significantly reduce blood glucose, reduce serum creatinine, reduce urea nitrogen levels and urine protein levels, and reduce kidney index in STZ-induced diabetic nephropathy model rats. At the same time, the ligustrazine nitrone derivatives can significantly reduce the incidence of diabetic retinopathy.

In the present invention, a new use of the ligustrazine nitrone derivatives has been found in the manufacture of medicaments for the prevention and treatment of a disease of diabetic complications. The compounds TBN and TN-2 of the present invention are provided by coupling of the derivatives of tetramethylpyrazine and nitrone groups, and the compounds have both the activities of anti-oxidation, anti-apoptosis, and anti-inflammatory of the derivatives of tetramethylpyrazine, and the strong radical scavenging activity of nitrone groups. While the efficacy of ligustrazine on diabetic nephropathy is retained, the therapeutic effects on hyperglycemia or free radical-induced oxidative damage have been improved. On the other hand, TBN and TN-2 have also shown certain therapeutic effects on diabetic retinopathy, and can delay the progression of diabetic nephropathy and diabetic retinopathy, to bring higher benefits to the patients.

The ligustrazine nitrone derivatives TBN and TN-2 of the present invention can be used in combination with the clinically available drugs in the treatment of diabetes and diabetic nephropathy, to synergistically improve the therapeutic effect, reduce the side effects of existing clinical drugs, and improve the benefit/risk ratio of the clinical drugs.

SUMMARY OF THE INVENTION

The present invention provided a new use of ligustrazine nitrone derivatives and pharmaceutical compositions thereof, namely, use of nitrone derivatives of tetramethylpyrazine in the preparation of a medicament and the prevention and treatment of a disease of diabetic complications. The derivatives have the structure of the following formula (I):

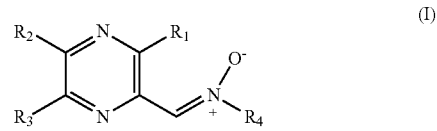

Wherein $R_1$ and $R_3$ are each independently C1-C6 alkyl; $R_2$ is C1-C6 alkyl or

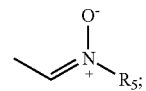

and $R_4$ and $R_5$ are each independently sec-butyl, isobutyl, t-butyl, cyclopentyl or cyclohexyl.

Preferably, the C1-C6 alkyl is methyl, ethyl, n-propyl, isopropyl, n-butyl, isobutyl, tert-butyl or n-pentyl.

Further preferably, the ligustrazine nitrone derivatives have a structure of the following formula:

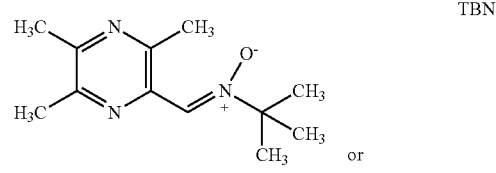

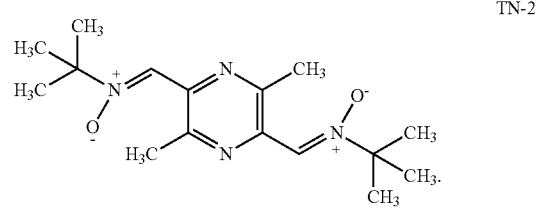

The present invention provides the use of the ligustrazine nitrone derivatives and pharmaceutical compositions thereof for the prevention and treatment of a disease of diabetic complications.

The disease of diabetic complications is preferably diabetic nephropathy and diabetic ophthalmopathy. Further preferably, the diabetic ophthalmopathy is retinopathy, glaucoma and cataract.

The present invention also provides the use of the ligustrazine nitrone derivatives and a pharmaceutical composition thereof for manufacturing a medicament, wherein the medicament can be used for preventing and treating diabetic nephropathy and its compositions. The pharmaceutical composition comprises a therapeutically effective amount of the ligustrazine nitrone derivative or a pharmaceutically acceptable salt thereof, and a pharmaceutically acceptable carrier.

The medicament containing the ligustrazine nitrone derivatives may be used alone or in combination with other drugs for preventing and treating a disease of diabetic complications.

The other drugs that can be used in combination are mainly oral antidiabetic drugs commonly used in clinical practice, including biguanides, sulfonylureas, glucosidase inhibitors, thiazolidinediones, non-sulfonylureas, and dipeptidyl peptidases inhibitors. Preferred drugs in the combination are angiotensin receptor blockers, angiotensin converting enzyme inhibitors and folic acid. Studies have shown that folic acid protects diabetic nephropathy by lowering homocysteine.

The ligustrazine nitrone derivatives can be formulated into various dosage forms with a pharmaceutical carrier, including tablets, granules, injections, powders, capsules, and suspensions.

Preferably, the therapeutically effective amount of the ligustrazine nitrone derivatives is from 0.001 to 2 g/kg body weight.

Table 1 in FIG. 5 lists the number of occurrences and time of appearance of retinopathy in diabetic nephropathy model rats.

DETAILED DESCRIPTION OF EMBODIMENTS

Some specific embodiments or examples of the present invention will be described below. It will be understood that these specific embodiments or examples are only used for further explanation of the invention, rather than to limit the scope of the inventive subject matters as defined by the claims.

EXAMPLE 1

Preparation and Grouping of STZ-Induced Diabetic Nephropathy Rat Model

1. Model Making

SD rats (200±10 g) were used as model animals, which were fasted for 12 h before injection. STZ was dissolved in citrate buffer at 1% concentration, and rats were fasted and intraperitoneally injected with 55 mg/kg STZ and placed in the cage, the rats being ensured with adequate water intake for 24 h. STZ injections need to be fast and complete within 10 minutes of injection. The normal control group was injected with an equal volume of pH 4.5 citric acid-sodium citrate buffer. The state of the animals (multiple drinking and polyuria) was observed. After 3 weeks of STZ injection, blood was collected from the tail vein, and fasting blood glucose>16.7 mmol/L was measured as the standard for diabetic nephropathy in rats.

2. Grouping

DKD rats were randomly assigned to 6 groups and given with different drugs. After 6 weeks of administration, the experiment was terminated and the protective effect of the drug on DKD rats was observed.

EXAMPLE 2

Effect of 1 Ligustrazine Nitrone Derivatives on Body Weight, Food Intake and Water Intake of STZ-Induced DKD Rats The general condition and body weight changes after rat modeling were observed weekly. The general conditions include the activity, mental state, coat color, diet, water intake and urine volume of the rats. The amount of water and the amount of feed were recorded weekly.

Figure 1:
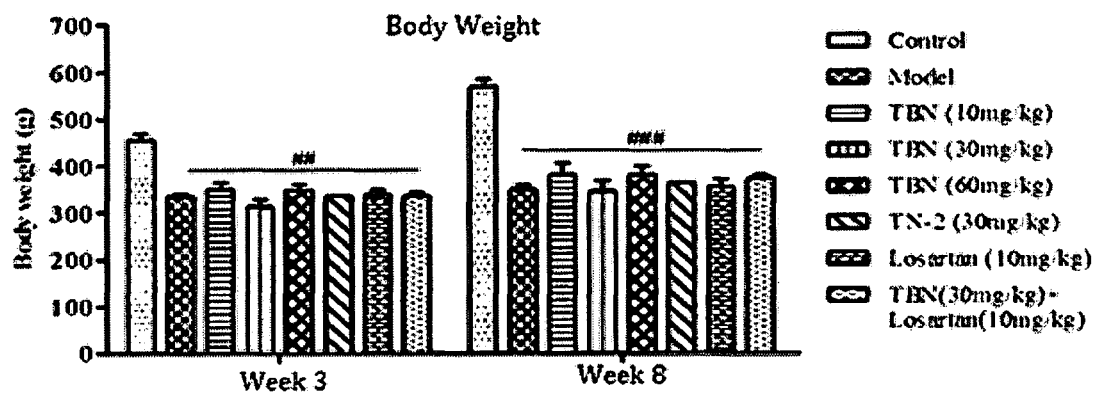
FIG. 1 shows the effect of ligustrazine nitrone derivatives on body weight (FIG. 1a), water intake (FIG. 1b), and food intake (FIG. 1c) of STZ-induced DKD rats. ###$P<0.001$, ##$P<0.01$ compared with the control group (Control); ***$P<0.001$,*$P<0.05$ compared with the model group (Model).
Figure 1:
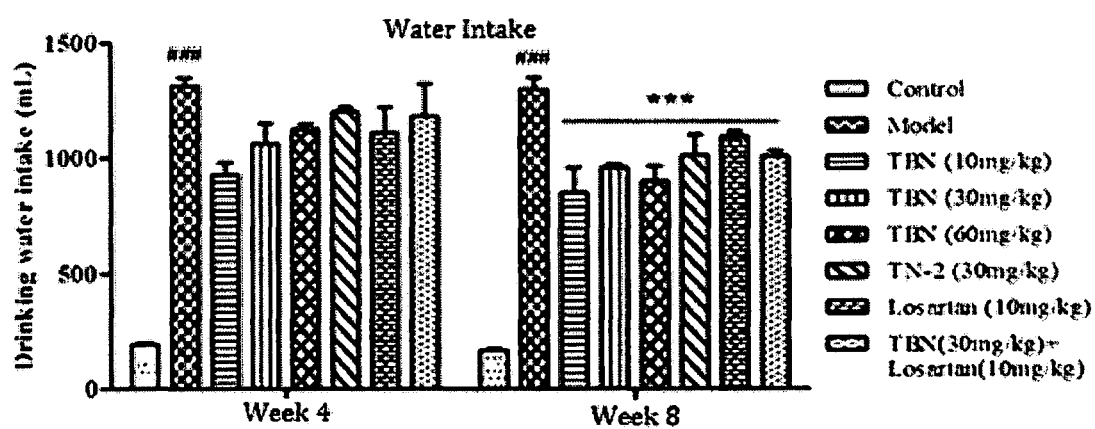
Figure 1:
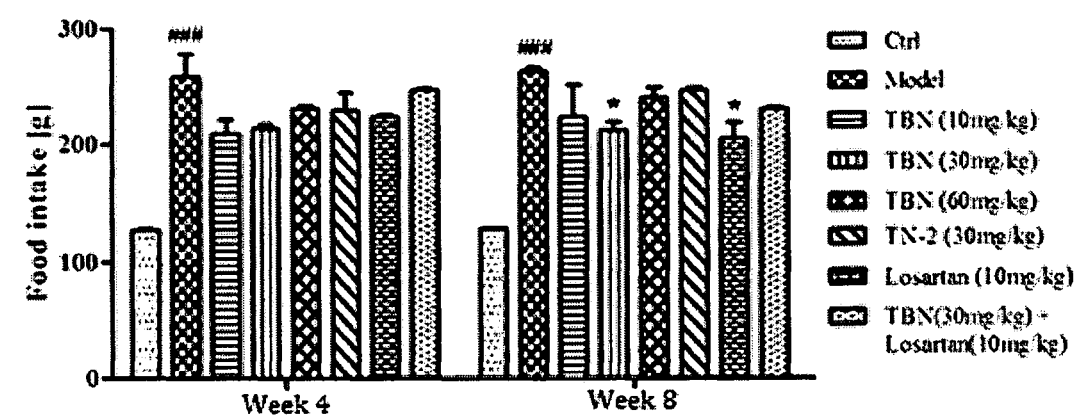

The effect of ligustrazine nitrone derivatives on the body weight of rats with STZ-induced diabetic nephropathy is shown in FIG. 1a. TBN and TN-2 have no effect on the body weight of rats with diabetic nephropathy. The changes of drinking water and feed volume in diabetic nephropathy rats are shown in FIG. 1b and FIG. 1c. The DKD rats in the TBN and TN-2 treatment groups had significantly lower water intake and food intake than the model group, indicating that TBN and TN-2 can slow the progression of diabetic disease in DKD rats, thereby improve the diabetic symptoms of more water and food intake of the DKD rats.

EXAMPLE 3

Effect of 1 Ligustrazine Nitrone Derivatives on Retinopathy of the STZ-Induced DKD Rats During the experiment, the retinopathy of rats was observed during daily administration, and the dates of retinopathy in different groups of rats were recorded.

Retinopathy is one of the common complications of diabetic nephropathy and has a high correlation with diabetic nephropathy. The effect of ligustrazine nitrone derivatives on STZ-induced retinopathy of DKD rats is shown in Table 1. The number of retinopathy in DKD rats after TBN and TN-2 treatment was reduced, and the time when retinopathy occurred is relatively delayed. The results indicate that the ligustrazine nitrone derivatives TBN and TN-2 can reduce and delay the occurrence of retinopathy.

EXAMPLE 4

Effect of Ligustrazine Nitrone Derivatives on Blood Glucose and Urine Protein in DKD Rats Induced by STZ During the experiment, the blood glucose of the rats was monitored after the completion of the modeling and after the completion of the administration, and urine protein was collected once at 24 hour.

Figure 2:
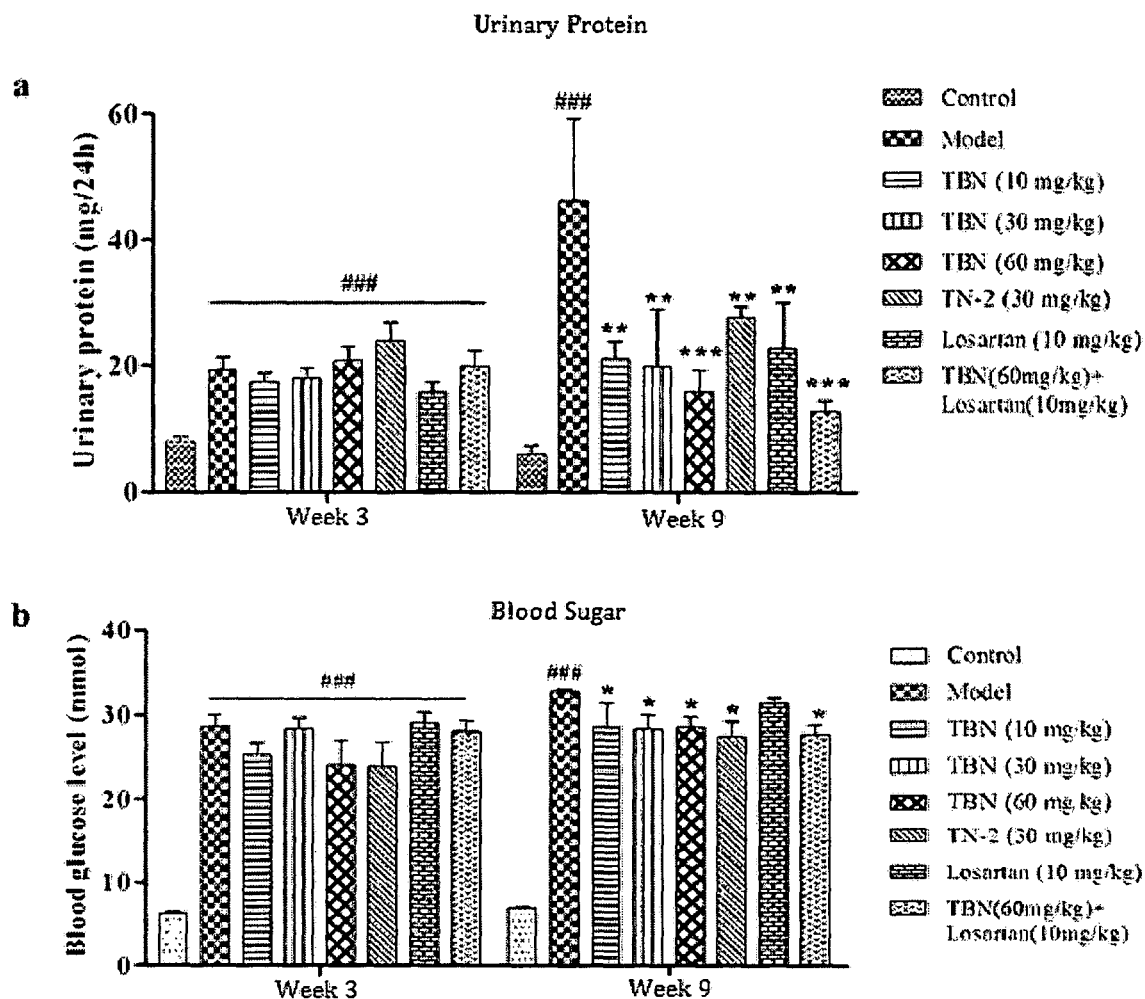
FIG. 2 shows the effect of ligustrazine nitrone derivatives on urinary protein (FIG. 2a) and rat blood glucose (FIG. 2b) of STZ-induced DKD rats. ###$P<0.001$ compared with the control group (Control);*$P<0.001$,$P<0.05$,*$P<0.01$ compared with the model group (Model).

The effect of ligustrazine nitrone derivatives on blood glucose of STZ-induced DKD rats is shown in FIG. 2a. The blood glucose was significantly increased after 3 weeks of STZ induction, and was significantly decreased after 6 weeks of treatment with TBN and TN-2. The effect of TBN and TN-2 on urinary protein of STZ-induced DKD rats is shown in FIG. 2b. Urinary protein content in urine of DKD rats treated with TBN and TN-2 was significantly reduced. The combined use of TBN and losartan is superior to treatment with TBN alone or losartan alone.

EXAMPLE 5

Effect of Ligustrazine Nitrone Derivatives on Serum Biochemical Parameters of STZ-Induced DKD Rats Six weeks after the administration, the rats were anesthetized, and the blood was taken from the abdominal aorta, and, after standing for 1 hour, was centrifuged at 3000 rmp for 10 min and stored at −70° C. Serum levels of creatinine, urea nitrogen, cholesterol and triglycerides were measured using an automated biochemical analyzer.

Figure 3:
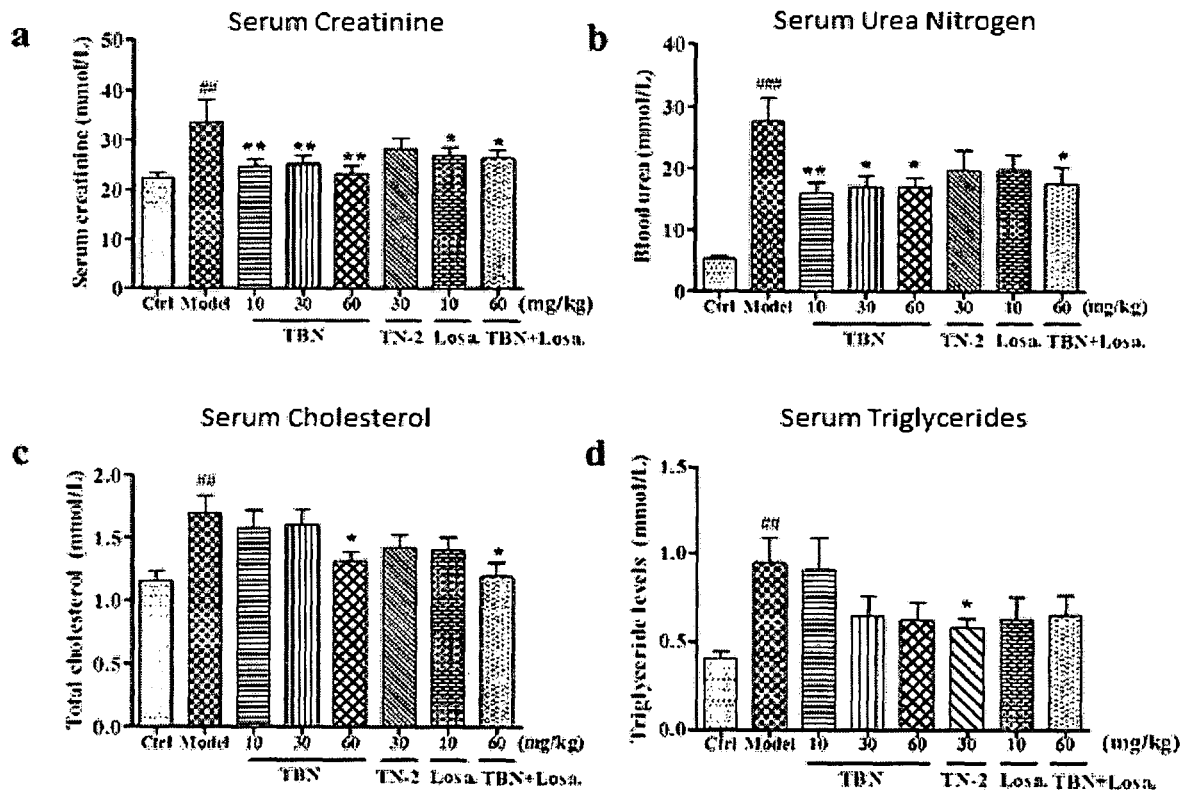
FIG. 3 shows the effect of ligustrazine nitrone derivatives on the levels of serum creatinine (FIG. 3a), urea nitrogen (FIG. 3b), cholesterol (FIG. 3c) and triglycerides (FIG. 3d) in STZ-induced DKD rats. ###$P<0.001$, ##$P<0.01$ compared with the control group (Control);**$P<0.05$,*$P<0.01$ compared with the model group (Model).

Serum creatinine, urea nitrogen, cholesterol and triglyceride levels may reflect the body's lipid metabolism, carbohydrate metabolism and kidney function. The effect of ligustrazine nitrone derivatives on serum creatinine, urea nitrogen, cholesterol and triglycerides in STZ-induced DKD rats is shown in FIG. 3. TBN and TN-2 can significantly reduce serum creatinine (FIG. 3a), urea nitrogen (FIG. 3b), cholesterol (FIG. 3c) and triglyceride (FIG. 3d) levels, in a dose-dependent manner, showing improvement in lipid metabolism, carbohydrate metabolism and renal function in STZ-induced diabetic nephropathy rats.

EXAMPLE 6

Effect of Ligustrazine Nitrone Derivatives on Kidney Index of STZ-Induced DKD Rats After 6 weeks of administration, the kidney tissue was uniformly separated by an autoclave surgical instrument, and the saline was washed with normal saline. After the filter paper was blotted, the fine balance was weighed, and then stored in a refrigerator at −80° C. for use. Kidney index (relative to kidney weight) is kidney weight (mg)/body weight (g)=BW/KW.

Figure 4:
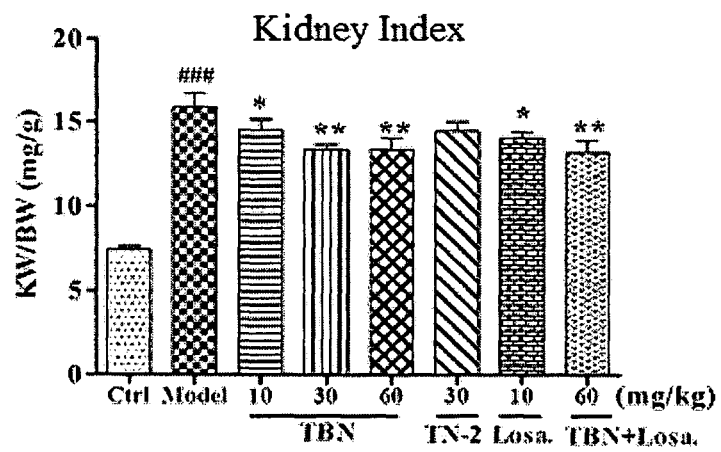
FIG. 4 shows the effect of ligustrazine nitrone derivatives on kidney index in STZ-induced DKD rats. ##$P<0.001$ compared with the control group (Control);**$P<0.05$, *$P<0.01$ compared with the model group (Model).

With the progress of pathological process of diabetic nephropathy, the glomerular basement membrane gradually thickens, the mesangium further widens, and focal tubular atrophy and interstitial fibrosis were finally developed with renal failure. The kidney index responds to, in certain extent, the pathological condition of diabetic nephropathy. The effect of ligustrazine nitrone derivatives on kidney index in STZ-induced DKD rats is shown in FIG. 4, TBN and TN-2 significantly reduced the kidney index of DKD rats, indicating that TBN and TN-2 can delay the progression of diabetic nephropathy.

The invention claimed is:

1. A method of treatment of a disease of diabetic complications, comprising administration of a therapeutically effectively amount of ligustrazine nitrone derivatives or a pharmaceutical composition thereof; the derivatives have a structure of formula (I):

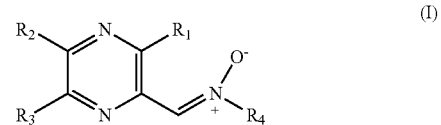

wherein, $R_1$ and $R_3$ are each independently C1-C6 alkyl; $R_2$ is C1-C6 alkyl or

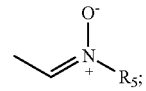

and $R_4$ and $R_5$ are each independently sec-butyl, isobutyl, t-butyl, cyclopentyl or cyclohexyl,
wherein the disease of diabetic complications is diabetic nephropathy.

2. The method according to claim 1, wherein the C1-C6 alkyl is methyl, ethyl, n-propyl, isopropyl, n-butyl, isobutyl, tert-butyl or n-pentyl.

3. The method according to claim 1, wherein the ligustrazine nitrone derivatives have a structure of formula:

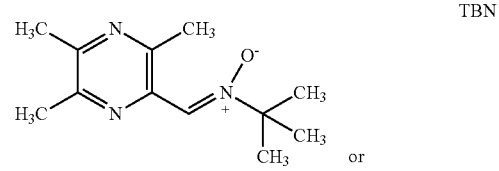

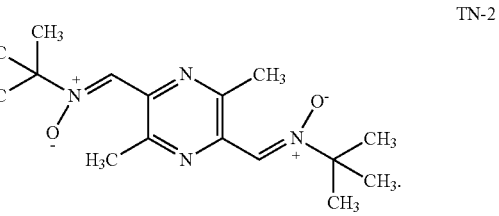

4. The method according to claim 1, wherein the pharmaceutical composition comprises a therapeutically effective amount of the ligustrazine nitrone derivative or a pharmaceutically acceptable salt thereof, and a pharmaceutically acceptable carrier.

5. The method according to claim 1, wherein the derivatives may be used alone or in combination with other drugs.

6. The method according to claim 5, wherein the other drugs are antihypertensive drugs.

7. The method according to claim 6, wherein the antihypertensive drugs are angiotensin receptor blockers, angiotensin converting enzyme inhibitors or folic acid.

8. The method according to claim 4, wherein the derivatives can be formulated into various dosage forms with a pharmaceutical carrier, the dosage forms comprising tablets, granules, injections, powders, capsules, or suspensions.

9. The method according to claim 1, wherein the therapeutically effective amount is from 0.001 to 2 g/kg.

* * * * *